US007041451B2

(12) United States Patent
Zhang et al.

(10) Patent No.: US 7,041,451 B2
(45) Date of Patent: *May 9, 2006

(54) ELECTROCHEMILUMINESCENCE HELICASE ASSAY

(75) Inventors: Litao Zhang, Collegeville, PA (US); Richard K Harrison, Glenmoore, PA (US)

(73) Assignee: sanofi-aventis, Bridgewater, NJ (US)

(*) Notice: Subject to any disclaimer, the term of this patent is extended or adjusted under 35 U.S.C. 154(b) by 427 days.

This patent is subject to a terminal disclaimer.

(21) Appl. No.: 10/187,212

(22) Filed: Jun. 28, 2002

(65) Prior Publication Data

US 2003/0032041 A1    Feb. 13, 2003

Related U.S. Application Data

(63) Continuation of application No. 09/410,960, filed on Oct. 5, 1999, now Pat. No. 6,448,004.

(51) Int. Cl.
*C12Q 1/68* (2006.01)
*C12P 19/34* (2006.01)
*C07H 21/00* (2006.01)
*C07H 21/02* (2006.01)
*C07H 21/04* (2006.01)

(52) U.S. Cl. ............... 435/6; 435/91.1; 435/91.2; 536/23.1; 536/24.3; 536/24.31; 536/24.32; 536/24.33

(58) Field of Classification Search ............ 435/6, 435/91.1, 91.2; 536/23.1, 24.3, 24.31, 24.32, 536/24.33
See application file for complete search history.

(56) References Cited

U.S. PATENT DOCUMENTS

| 4,568,649 A | 2/1986 | Bertoglio-Matte |
| 5,705,344 A | 1/1998 | Giordano et al. |
| 5,747,247 A | 5/1998 | Kowalczykowski et al. |
| 6,448,004 B1 * | 9/2002 | Zhang et al. ............. 435/6 |

FOREIGN PATENT DOCUMENTS

| WO | WO 93/12245 | 6/1993 |
| WO | WO 95/08644 | 3/1995 |

OTHER PUBLICATIONS

Mullins et al., Specific Synthesis of DNA in Vitro via a Polymerase-Catalyzed Chain Reaction, Methods in Enzymology, 155, 335-350 (1987).
Taylor et al., The Use of Phosphorothioate-Modified DNA In Restriction Enzyme Reactions to Prepare Nicked DNA, Nucleic Acids Research 13(24, 8749-8764 (1985).
Saiki et al., Enzymatic Amplification of B-Globin Genomic Sequences and Restriction Site Analysis for Diagnosis of Sickle Cell Anemia, Science, 230, 1350-1354 (1985).

Roman et al., Characterization of the Helicase Activity of the *Escherichia coli* RecBCD Enzyme Using a Novel Helicase Assay, Biochemistry 28(7), 2863-2873 (1989).
Kenten et al., Rapid Electrochemiluminescence Assays of Polymerase Chain Reaction Products, Clinical Chemistry 37(9), 1626-1632 (1991).
Kenten et al., Improved Electrochemiluminescent Label for DNA Probe Assays: Rapid Quantitative Assays of HIV-1 Polymerase Chain Reaction Products, Clinical Chemistry 38(6), 873-879 (1992).
Schutzbank et al., Detection of Human Immunodeficiency Virus Type 1 Proviral DNA by PCR Using an Electrochemiluminescence-Tagged Probe, Journal of Clinical Microbiology 33(8), 2036-2041 (1995).
Runyon et al., *Eischerichia coli* helicase II (UvrD) protein initiates DNA unwinding at nicks and blunt ends, Proc. Natl. Acad. Sci., 87, 6383-6387 (1990).
Sanger et al., DNA sequencing with chain-terminating inhibitors, Proc. Natl. Acad. Sci. 74(12), 5463-5467 (1977).
Matson, DNA Helicases of *Escherchia coli*, Progress in Nucleic Acid Research & Molecular Biology 40, 289-326 (1991).
Palas et al., Biochemical & Physical Characterization of Exonuclease V from *Eschericha coli*, The Journal of Biological Chemistry, 265(6), 3447-3454 (1990).
Matson et al., The Gene 4 Protein of Bacteriophage T7, The Journal of Biological Chemistry 258(22), 14017-14024 (1983).
LeBowitz et al., The *Escherichia coli* dnaB Replication Protein Is a DNA Helicase, The Journal of Biological Chemistry 261(10), 4738-4748 (1986).
Lohman et al., Mechanisms of Helicase-Catalyzed DNA Unwinding, Annu. Rev. Biochem. 65, 169-214 (1996).
Venkatesan et al., Bacteriophage T4 Gene 41 Protein, Required for the Synthesis of RNA Primers, Is Also a DNA Helicase, The Journal of Biological Chemistry, 257(20), 12426-12434 (1982).
Reha-Krantz et al., The dnaB Gene Product of *Escherichia coli*, The Journal of Biological Chemistry 253(11), 4043-4050 (1978).
Matson et al., DNA Helicases: Enzymes with Essential Roles in All Aspects of DNA Metabolism, BioEssays 16(1), 13-22 (1994).
Li et al., Three new DNA helicases from *Saccharomyces cerevisiae*, Chromosoma 102, S93-S99 (1992).

(Continued)

*Primary Examiner*—Jezia Riley
(74) *Attorney, Agent, or Firm*—Bell, Boyd & Lloyd PLLC

(57) ABSTRACT

The present invention relates to electrochemiluminescent assays for detecting helicase activity. The invention provides a helicase assay that is rapid, sensitive and suitable for high throughput screening for helicase inhibitors. Helicase inhibitors represent a class of pharmacological agents useful for the treatment of disease.

8 Claims, 8 Drawing Sheets

OTHER PUBLICATIONS

Bruno, Broad applications of electrochemiluminescence technology to the detection and quantiation of microbiological, biochemical and chemical analytes, Recent Res. Devel. in Microbiology 1, 25-46 (1997).

Blackburn Gary F. et al., Electrochemiluminescence Detection for Development of Immunoassays and DNA Probe Assays for Clinical Diagnostics, Clin. Chem. 37(9):1534-1539 (1991).

Earnshaw David L. et al., Time-Resolved Fluorescence Energy Transfer DNA Helicase Assays for High Throughput Screening, Journal of Biomol. 4(5):239-247 (1999).

Kyono Kiyoshi et al., Detection of Hepatitis C Virus Helicase Activity Using the Scintillation Proximity Assay System, Analytical Biochemistry 257:120-126 (1998).

* cited by examiner

SEQUENCE LISTING

```
<160> NUMBER OF SEQ ID NOS: 6

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide used in traditional helicase assay

<400> SEQUENCE: 1
tttttttttt tttttttttt tttttttttt gttaaaggcc gcttttgcgg gatcgtcacc        60

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide used in fluorescence quenching helicase assay

<400> SEQUENCE: 2
gtgacgatcc cgcaaaagcg gcctttaact ccctgcaagc ctcagcgacc gaatatatcg        60

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide used in fluorescence quenching helicase assay

<400> SEQUENCE: 3
tttttttttt tttttttttt tttttttttt tgttaaaggc cgcttttgcg ggatcgtcca        60

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence:
      Oligonucleotide used in electrochemiluminescence helicase assay

<400> SEQUENCE: 4
tttttttttt tttttttttt tttttttttt gttaaaggcc gcttttgcgg gatcgtcacc        60

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide used in electrochemiluminescence helicase assay

<400> SEQUENCE: 5
gttaaaggcc gcttttgcgg gatcgtcacc                                         30

<210> SEQ ID NO 6
<211> LENGTH: 33
<212> TYPE: DNA
<213> ORGANISM: Artificial Sequence
<220> FEATURE:
```

```
<223> OTHER INFORMATION: Description of Artificial Sequence:
      Oligonucleotide used in electrochemiluminescence helicase assay

<400> SEQUENCE: 6
ggtgacgatc ccgcaaaagc ggcctttaac agc                                    33
```

ELECTROCHEMILUMINESCENCE HELICASE ASSAY

This application is a continuation of U.S. Ser. No. 09/410,960, filed 5 Oct. 1999, now U.S. Pat. No. 6,448,004, herein incorporated by reference in entirety.

FIELD OF THE INVENTION

The present invention relates to assays which use electrochemiluminescence for the detection of helicase activity. Therefore, the invention provides a helicase assay that is rapid, sensitive and suitable for high throughput screening for helicase activity in general, and especially for potential helicase inhibitors. Helicase inhibitors represent a class of pharmacological agents useful for the treatment of disease.

BACKGROUND OF THE INVENTION

DNA Helicases

DNA helicases are enzymes that are involved in all aspects of nucleic acid metabolism (Lohman and Bjornson, *Annu. Rev. Biochem.,* 1996, 65, 169–214; Matson, S. W., *Progress in Nuclear Acid Research and Molecular Biology,* 1991, 40, 289–326). The stable form of most DNA in vivo is double stranded helical DNA. Single stranded DNAs are required for DNA replication, repair, recombination and conjugation. In order to form single stranded DNA from a double strand, the DNA duplex must be at least partially unwound and separated. Unwinding of stable duplex DNAs is catalyzed by DNA helicases using the energy derived from the hydrolysis of nucleoside 5'-triphosphates (NTP). Helicase enzymes translocate along DNA to unwind (unhybridize) the duplex stands at a rate that can be as fast as 500–1000 bp/s.

DNA helicases have been identified in various prokaryotes, eukaryotes, bacteriophages and viruses. Most organisms encode multiple helicases. For example, *E.coli* encodes at least 12 different helicases (Matson, et al., *BioEssays,* 1994, 16, 13–22) and *S. cerevisiae* encodes at least six helicase forms (Li, et al., *Chromosoma,* 1992, 102, S93–S99). Although these DNA helicases play many different functions in DNA metabolism, it is now clear that helicase activity is the function ascribed to unwinding the DNA duplex. Due to the essential function of helicases for cellular metabolism, these enzymes represent important targets for developing therapeutic agents.

Helicase Assays

Several types of assays have been developed to measure the unwinding of duplex nucleic acids by helicases. One such assay measures the sensitization of labeled duplex DNA to single-strand specific nucleases, such as S1 or exonuclease I, resulting in the production of ssDNA during unwinding (Palas et al., *J. Biol. Chem.,* 1990 265:3447). Electron microscopy has also been employed to visualize directly regions of DNA unwound by proteins such as recBCD enzyme, rep protein, *E. coli* helicases I and II, and SV40 T antigen (Runyon et al., *Proc. Natl. Acad. Sci.,* 1990, 87:6383).

The most common assay for determining helicase activity in vitro utilizes electrophoresis (Venkatesan et al., *J. Biol. Chem.,* 1982, 257, 12426; Matson, et al., *J. Biol. Chem.,* 1983, 258, 14017). Helicase enzyme unwinds duplex DNA yielding single stranded DNAs. The products of this reaction are resolved on a polyacrylamide or agarose gel. A radioactive label within the DNA permits direct visualization and quantitation of the results.

A continuous spectrophotometric assay developed for studying recBCD enzyme helicase activity utilizes a ssDNA binding protein, either *E. coli* SSB protein (single-strand DNA binding protein) or phage T4 gene 32 protein, as the reporter molecule (Roman et al., *Biochemistry,* 1989, 28:2863). As dsDNA is unwound, the SSB protein binds to the ssDNA formed, resulting in quenching of its intrinsic fluorescence. Additional helicase assays are described in U.S. Pat. Nos. 4,568,649, 5,705,344 and 5,747,247.

Each of these assays described above have certain limitations relating to sensitivity, number of steps required to perform the assay, and/or the limited number of samples that can be tested. Obviously, such methods are not readily adaptable for highly sensitive, high-throughput drug screening formats. Therefore, there is a need in the art for a simple, yet sensitive helicase assay that can be performed in high throughput. The present invention overcomes these obstacles, and provides a helicase assay that is rapid, sensitive and suitable for a high throughput screening for potential helicase inhibitors.

Electrochemiluminescence Assays

Electrochemiluminecence is light generated when a low voltage is applied to an electrode, thereby triggering a cyclic oxidation and reduction reaction of ruthenium metal ion bound in a chelate of tris-(bipyridine). This technology has broad applicability to detection of microbiological, biochemical and chemical analytes (Bruno et al., 1997, *Rec. Res. Devel. In Micro.* 1:25).

Electrochemiluminescent labels for DNA have been developed (Kenten et al., 1991, *Clin. Chem.* 37:1626; Kenten et al., 1992, *Clin. Chem.* 38:873; Origen® label, Origen® Phosphoramidite and TAG Phosphoramidite available from IGEN Inc., Rockville, Md.), and used for detection of polymerase chain reaction products (Schutzbank et al., 1995, *J. Clin. Microbiol.,* 33:2023). These assays have been shown to be rapid and effective for the detection of amplified PCR products.

The citation of any reference herein should not be construed as an admission that such reference is available as "Prior Art" to the instant application.

SUMMARY OF THE INVENTION

The present invention provides a helicase assay that is rapid, sensitive and suitable for high throughput screening for potential helicase inhibitors. Helicase inhibitors represent a class of pharmacological agents useful for the treatment of disease.

Therefore, in a first embodiment, the present invention provides an electrochemiluminescent assay method for detecting helicase activity in a sample, the method comprising (a) combining the sample with a first nucleic acid or nucleic acid molecule comprising an electrochemiluminescent label and hybridized to a complementary second nucleic acid or nucleic acid molecule;

(b) incubating the sample and hybridized nucleic acids or nucleic acid molecules from step (a) under conditions where helicase present in the sample can unhybridize the first and second nucleic acids or nucleic acid molecules;

(c) capturing unhybridized first nucleic acid or nucleic acid molecule; and (d) measuring electrochemiluminescence from the captured first nucleic acid or nucleic acid molecule.

The helicase may be a human or pathogenic helicase. Preferably, the helicase is a fungal, viral, bacterial or parasitic helicase.

Any method for capturing unhybridized first nucleic acid or nucleic acid molecule may be employed. In a preferred series of steps, between steps (b) and (c) above, the unhybridized nucleic acids or nucleic acid molecules are incubated with a third nucleic acid or nucleic acid molecule complementary to the first nucleic acid or nucleic acid molecule and comprising a capturing ligand, under conditions where the first and third nucleic acids or nucleic acid molecules can hybridize. Thereafter, the hybridized first and third nucleic acids or nucleic acid molecules may be captured with a capturing receptor which binds the capturing ligand. The capturing receptor may be on the surface of magnetic beads. In a preferred embodiment, the capturing ligand is biotin and the capturing receptor is avidin. The preferred electrochemiluminescent label is a ruthenium chelate.

In another embodiment, the present invention relates to a method for detecting in a sample an agent that modulates helicase activity by
  (a) combining the sample, a helicase and a first nucleic acid or nucleic acid molecule comprising an electrochemiluminescent label and hybridized to a complementary second nucleic acid or nucleic acid molecule, thereby forming a mixture;
  (b) incubating the mixture from step (a) under conditions where the helicase can unhybridize the first and second nucleic acids or nucleic acid molecules in the absence of the sample;
  (c) capturing unhybridized first nucleic acid or nucleic acid molecule; and
  (d) measuring electrochemiluminescence from the captured first nucleic acid or nucleic acid molecule.

In a preferred embodiment, the agent is an inhibitor of helicase activity. The helicase may be a human or pathogenic helicase. Preferably, the helicase is a fungal, viral, bacterial or parasitic helicase.

Any method for capturing unhybridized first nucleic acid or nucleic acid molecule may be employed. In a preferred series of steps, between steps (b) and (c) above, the unhybridized nucleic acids or nucleic acid molecules are incubated with a third nucleic acid or nucleic acid molecule complementary to the first nucleic acid or nucleic acid molecule and comprising a capturing ligand, under conditions where the first and third nucleic acids or nucleic acid molecules can hybridize. Thereafter, the hybridized first and third nucleic acids or nucleic acid molecules may be captured with a capturing receptor which binds the capturing ligand. The capturing receptor may be on the surface of magnetic beads. In a preferred embodiment, the capturing ligand is biotin and the capturing receptor is avidin. The preferred electrochemiluminescent label is a ruthenium chelate.

In still another embodiment, the invention provides kits for electrochemiluminescent detection of helicase activity. Such kits comprise
  (a) a first nucleic acid or nucleic acid molecule comprising an electrochemiluminescent label;
  (b) a second nucleic acid or nucleic acid molecule complementary to the first nucleic acid or nucleic acid molecule;
  (c) a helicase and/or magnetic beads suitable for facilitating electrochemiluminescence detection.

In one aspect, the first nucleic acid or nucleic acid molecule is already hybridized to the second nucleic acid or nucleic acid molecule. The kits according to the invention may further comprise a third nucleic acid or nucleic acid molecule complementary to the first nucleic acid or nucleic acid molecule and comprising a capturing ligand. Under such circumstances, the kit will, in general, include a capturing receptor capable of binding the capturing ligand. In a preferred embodiment, the capturing receptor is on the surface of magnetic beads. In a most preferred embodiment, the capturing ligand is biotin and the capturing receptor is avidin.

A 60 bp oligonucleotide was labeled with $^{32}P$ at 3' end. Then a complementary 60 bp oligonucleotide was hybridized with the labeled nucleotide. Various amounts of DnaB helicase as indicated were added, and the reaction mixtures were incubated at 37° C. for 30 min. EDTA was added to stop the reaction, and the samples were separated on a PAGE gel and detected by autoradiography. Lane 8 contains a boiled sample to show separation of ssDNA and ds DNA. Lane 9 contains only labeled ssDNA.

Figure 2:
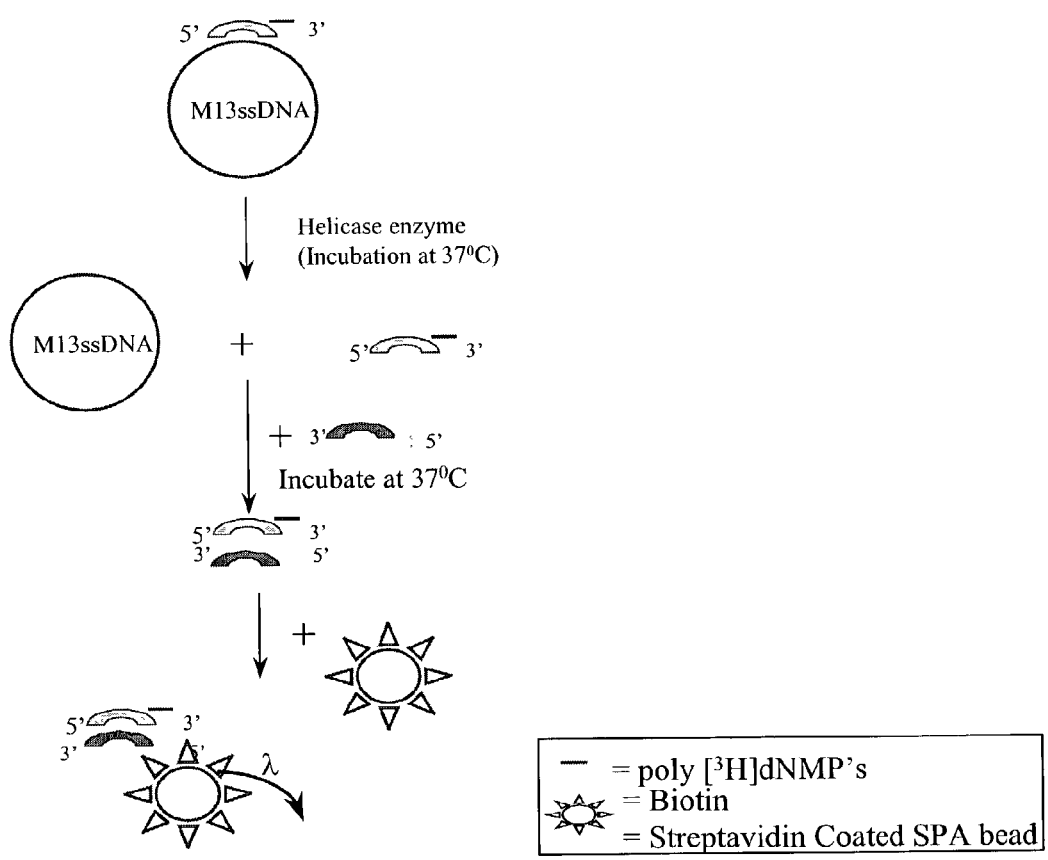

FIG. 2: Schematic of the Scintillation Proximity Assay (SPA) for quantitation of helicase activity using $^3H$-radiolabled oligonucleotides and M13 ssDNA.

Figure 3:
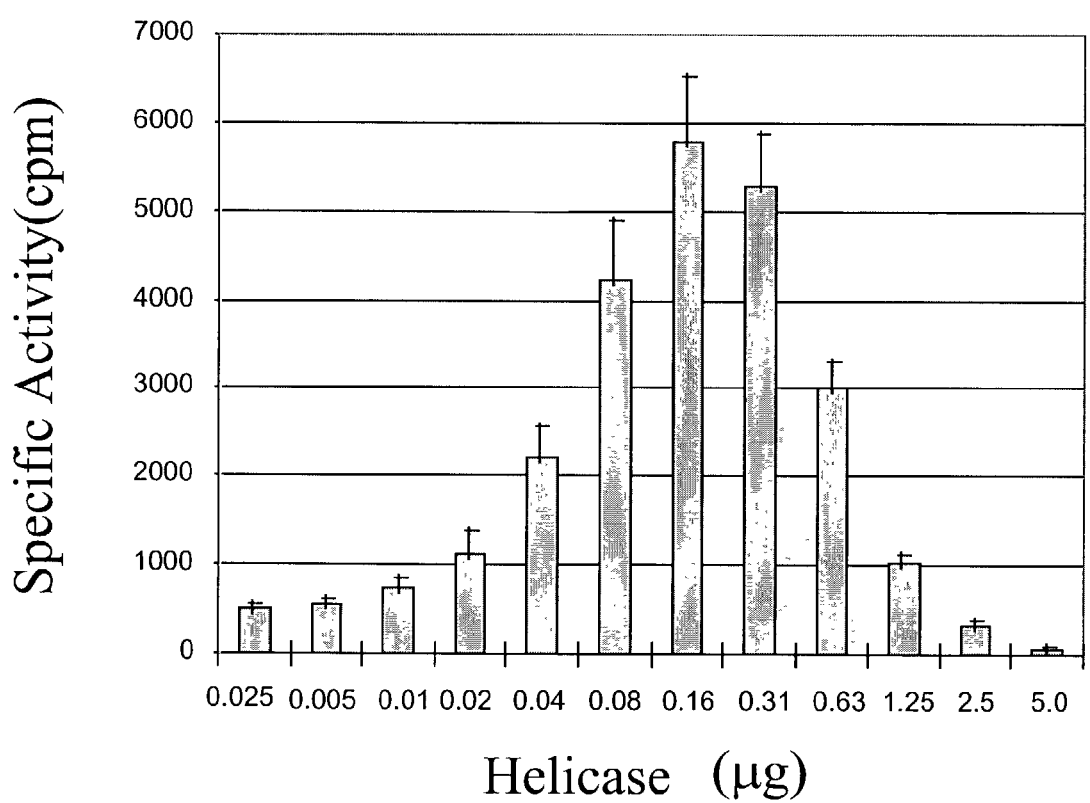

FIG. 3: Unwinding of $^3H$-substrates using varying amount of DnaB helicase. The counts per minute(cpm) is plotted as function of the amount of DnaB helicase added in each reaction.

Figure 4:
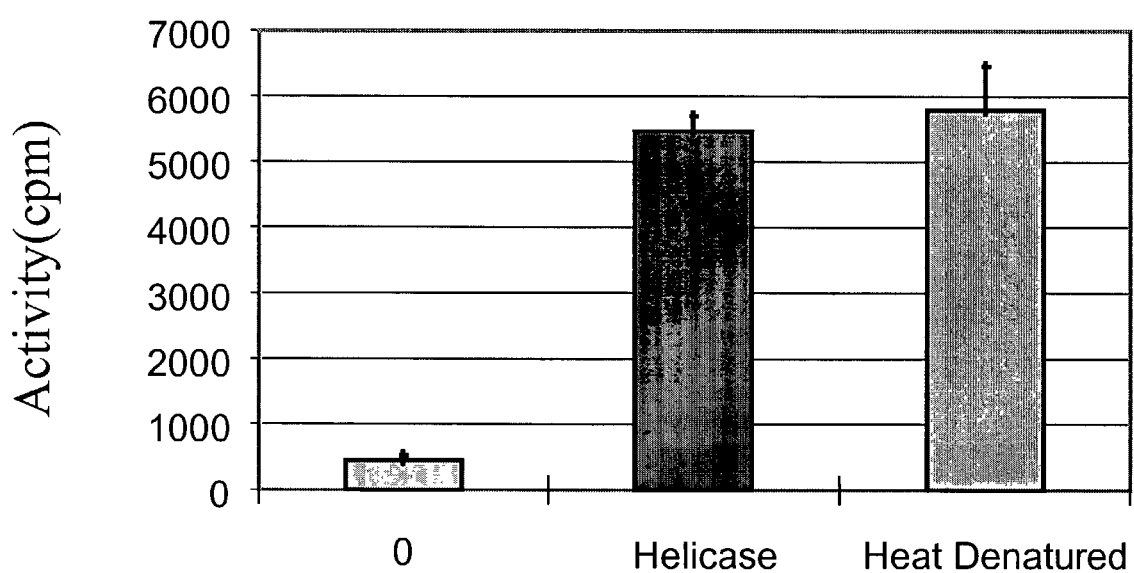

FIG. 4: Bar graph of DnaB helicase activity using SPA assay.

Figure 5:
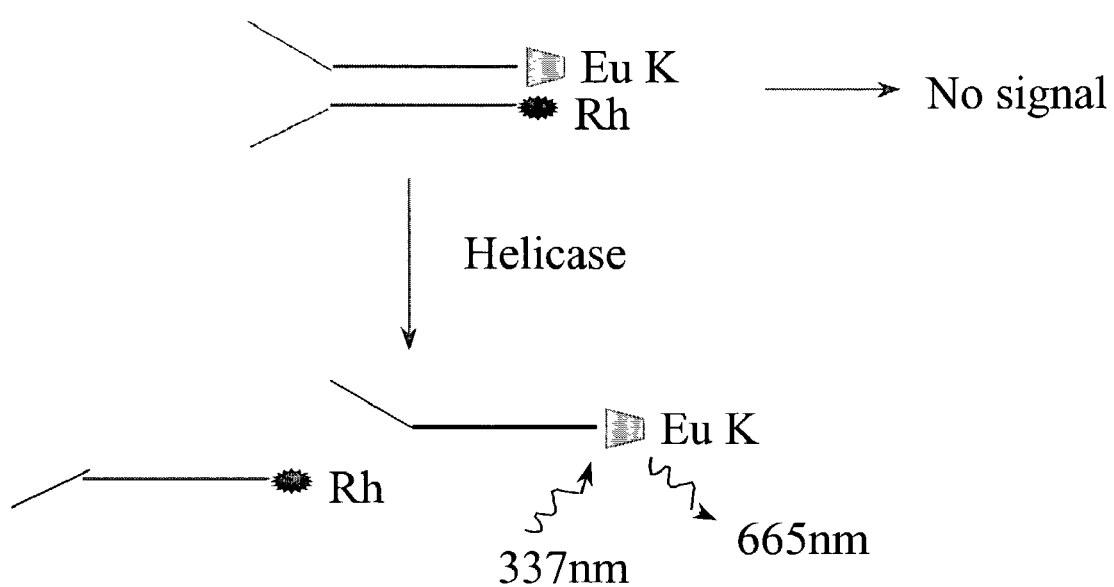

FIG. 5: Schematic of Time Resolved Flourecence Quenching Assay for quantitation of helicase activity using Eu-radiolabeled oligonucleotides and a Rhodamine labeled complementary oligonucleotides.

Figure 6:
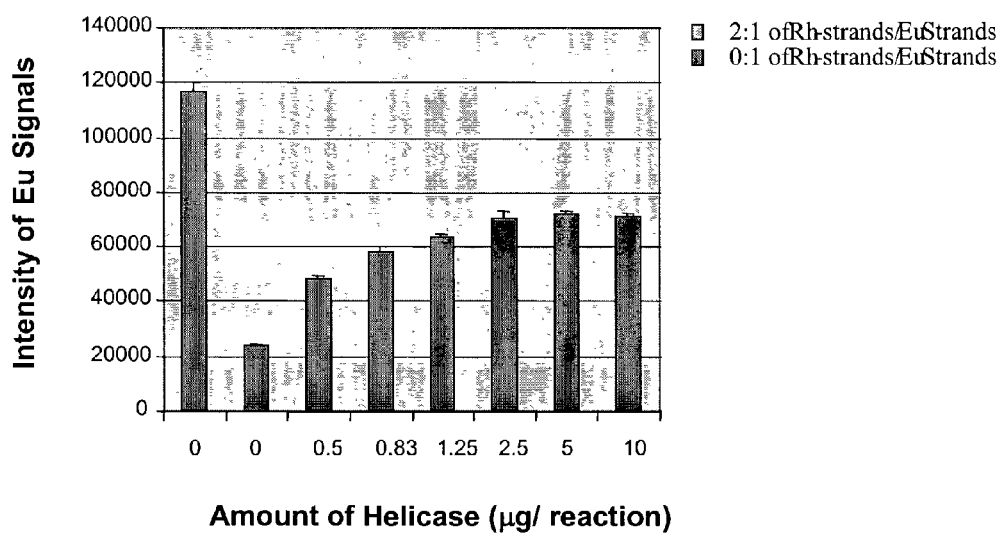

FIG. 6: Unwinding of hybridized substrates using varying amounts of DnaB helicase. The amount of Fluorescence released from unwinding dsDNA is plotted as function of the amount of DnaB helicase added in each reaction.

Figure 7:
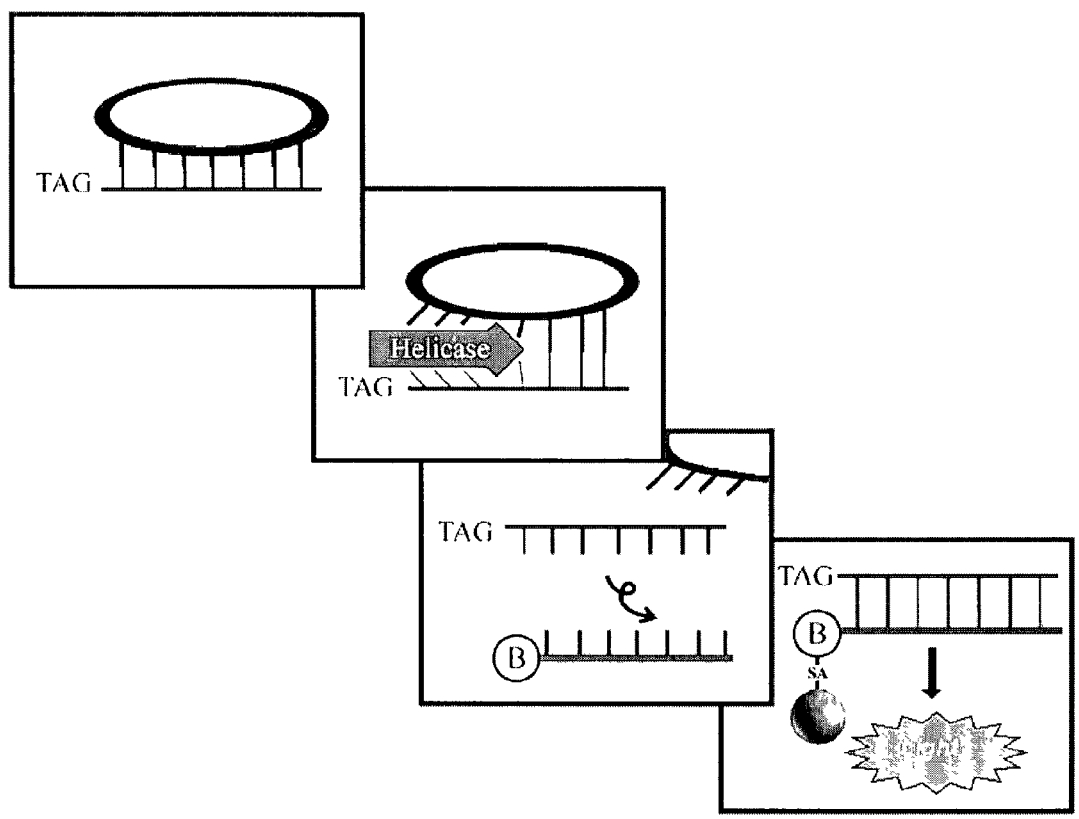

FIG. 7: Schematic of electrochemiluminescence (ECL) assay for quantitation of helicase activity using Ruthenium labeled oligonucleotides and M13 ssDNA.

Figure 8:
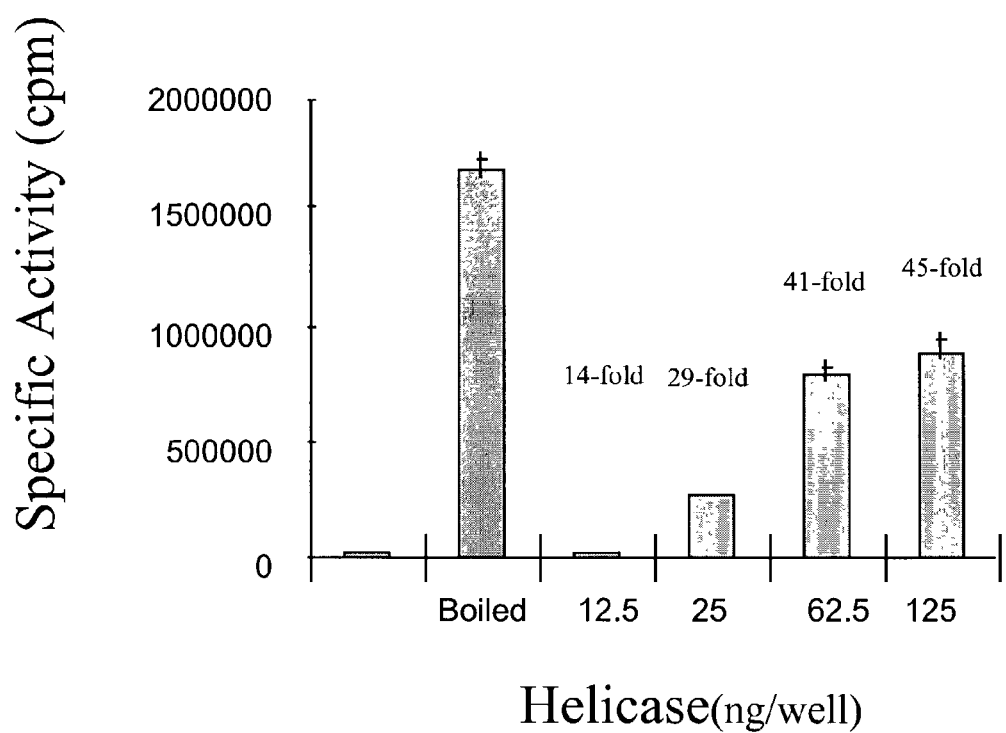

FIG. 8: Electrochemiluminesent signal generated by unwinding double stranded substrates using varying amounts of DnaB helicase. The ECL signal is plotted a function of the amount of helicase added to the reaction.

DETAILED DESCRIPTION OF THE INVENTION

The present invention advantageously provides an electrochemiluminescent assay method for detecting helicase activity, and a method for identifying modulators of helicase activity. Therefore, the present invention provides a rapid and sensitive assay for potential helicase inhibitors that is suitable for high throughput screening. The invention also provides kits for use in identifying helicase activity, and screening for potential modulators of helicase activity. Such kits include premeasured amounts of the components used in the disclosed methods.

Since helicases are necessary for a wide variety of cellular functions including growth, target diseases are limited only in that disease or disease progression be subject to inhibition by modulation of the activity of one or more specific helicases. As such, target diseases include viral, bacterial and fungal infections, metabolic disease, genetic disease, cell growth and regulatory disfunction, such as neoplasia, inflammation, hypersensitivity, etc. The target diseases may be afflictions of plants, especially agricultural crops, or animals, especially livestock, domestic animals and humans.

The various aspects of the invention will be set forth in greater detail in the following sections. This organization into various sections is intended to facilitate understanding of the invention, and is in no way intended to be limiting thereof.

Definitions

The following defined terms are used throughout the present specification, and should be helpful in understanding the scope and practice of the present invention.

In a specific embodiment, the term "about" or "approximately" means within 20%, preferably within 10%, and more preferably within 5% of a given value or range.

As used herein, the articles "a" and "an" mean one or more; hence, "a helicase" is meant to include assays involving one of more helicases, such as simultaneous screens for inhibitors of several helicases.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as an oligonucleotide, a cDNA, genomic DNA, or RNA, when a single stranded form of the nucleic acid molecule can anneal to the other nucleic acid molecule under the appropriate conditions of temperature and solution ionic strength. The conditions of temperature and ionic strength determine the "stringency" of the hybridization. Low stringency hybridization conditions correspond to a $T_m$ of 55°, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook, Fritsch & Maniatis, *Molecular Cloning: A Laboratory Manual*, Second Edition (1989) Cold Spring Harbor Laboratory Press, Cold Spring Harbor, N.Y., 9.50–0.51). For hybridization with shorter nucleic acids, i.e., oligonucleotides, the position of mismatches becomes more important, and the length of the oligonucleotide determines its specificity (see Sambrook et al., 11.7–11.8). Preferably a minimum length for a hybridizable nucleic acid is at least about 10 nucleotides; preferably at least about 15 nucleotides; and more preferably the length is at least about 20 nucleotides.

As used herein, the term "oligonucleotide" refers to a nucleic acid, generally of at least 18 nucleotides, that is hybridizable to a complementary nucleic acid. Oligonucleotides can be labeled, e.g., with $^{32}P$-nucleotides or nucleotides to which a label, such as biotin or ruthenium chelate, has been covalently conjugated. Generally, oligonucleotides are prepared synthetically, preferably on a nucleic acid synthesizer. Accordingly, oligonucleotides can be prepared with non-naturally occurring phosphoester analog bonds, such as thioester bonds, etc.

"Avidin" is a meant to include any protein or polypeptide capable of high affinity binding to biotin. Streptavidin is one such example of avidin.

A "helicase" is any protein or polypeptide having the ability to unwind (unhybridize) a duplex of complementary nucleic acids or nucleic acid molecules.

Helicase Assays

The methods defined by the present invention involve forming a mixture of a first nucleic acid or nucleic acid molecule comprising an electrochemiluminescent label and hybridized to a complementary second nucleic acid or nucleic acid molecule. The hybridized first and second nucleic acids or nucleic acid molecules may be RNA or DNA, linear or circular, depending on the specificity of the targeted helicase. In addition, other nucleic acids or nucleic acid molecules or structural analogs may be substituted so long as they provide an active substrate for the targeted helicase activity. The nucleic acids or nucleic acid molecules may be of any length amenable to the assay conditions and requirements. For example, ensuring helicase substrate specificity and minimizing non-specific renaturation requires a minimal region of complementarity between the first and second nucleic acids or nucleic acid molecules, typically at least about 12, more typically at least about 18 and preferably at least about 24 continuous base pairs. There may be a size differential between the strands. The sizes are selected to facilitate the assay and to provide statistically significant assay results; frequently the sizes will differ by at least one or two orders of magnitude. In general, optimal lengths are readily determined empirically.

The nucleic acids or nucleic acid molecules may be of any sequence which provides a convenient substrate for the targeted helicase(s). The nucleic acids or nucleic acid molecules may be complementary over the entire length of at least one of the nucleic acids or nucleic acid molecules or there may be regions of noncomplementary 5' and/or 3' of the complementary region. Introducing these 5' and/or 3' noncomplementary regions provides molecular forks that yield better substrates for some helicases. Generally, conveniently replicated vectors e.g. phage, or restriction fragments thereof, provide an inexpensive source of the nucleic acids or nucleic acid molecules. The assays are generally compatible with the presence of DNA binding proteins, such as histones. It is often advantageous to include a variety of potential substrates, e.g. double-stranded nucleic acids of varied size, sequence, protein complexing, etc. to improve the likelihood of detecting substrate-sensitive helicases.

The first nucleic acid or nucleic acid molecule comprises a detectable electrochemiluminescent label. Electrochemiluminecence is light generated when a low voltage is applied to an electrode, thereby triggering a cyclic oxidation and reduction reaction of the label. Any electrochemiluminescent label capable of such cyclic oxidation/reduction and light generation may be used according to the present invention. The preferred label is ruthenium metal ion bound in a chelate of tris-(bipyridine). Specific electrochemiluminescent labels for DNA have been developed (Kenten et al., 1991, *Clin. Chem.* 37:1626; Kenten et al., 1992, *Clin. Chem.* 38:873; Origen® label, Origen® phosphoramidite and TAG phosphoramidite, IGEN Inc., Rockville, Md.) and are most preferred for the present invention.

Any pathogenic helicase (i.e. any helicase capable of acting harmfully to a host cell or organism) may be analyzed according to the present invention. Rapidly growing cells (e.g. in neoplasia) may be targeted by inhibitors of human helicases, especially replicative helicases. In addition, pathogen-selective or -specific helicases are used to identify pharmacological therapeutics for the treatment of infectious disease. Fungal, viral, bacterial and parasitic helicases, in particular, provide medically urgent targets for identifying inhibitors by the present methods. Alternatively, a plurality of helicases or panel comprising a preselected range of different helicases can be used to maximize the scope of the assay.

Preferred pathogenic helicases are derived from medically significant infectious fungi, such as *Aspergillus, Candida* species; bacteria such as *Staphylococci* (e.g *aureus*), *Streptococci* (e.g. *pneumoniae*), *Clostridia* (e.g. *perfringens*), *Neisseria* (e.g *gonorrhoeae*), *Enterobacteriaceae* (e.g. *coli*), *Helicobacter* (e.g *pylori*), *Vibrio* (e.g. *cholerae*), *Capylobacter* (e.g. *jejuni*), *Pseudomonas* (e.g *aeruginosa*), *Haemophilus* (e.g. *influenzae*), *Bordetella* (e.g. *pertussis*), *Mycoplasma* (e.g. *pneumoniae*), *Ureaplasma* (e.g. *urealyticum*), *Legionella* (e.g. *pneumophila*), *Spirochetes* (e.g. *Treponema, Leptospira* and *Borrelia*), *Mycobacteria* (e.g. *tuberculosis, smegmatis*), *Actinomycies* (e.g. *israelii*), *Nocardia* (e.g. *asteroides*), *Chlamydia* (e.g. *trachomatis*), *Rickettsia, Coxiella, Ehrilichia, Rochalimaea, Brucella, Yersinia, Fracisella,* and *Pasteurella*; protozoa such as sporozoa (e.g. *Plasmodia*), rhizopods (e.g. *Entamoeba*) and flagellates (*Trypanosoma, Leishmania, Trichomonas Giardia*, etc.); and viruses such as (+) RNA viruses (examples include Picomaviruses, e.g. polio; Togaviruses, e.g. rubella; Flavivimses, e.g. HCV; and Coronaviruses), (−) RNA viruses (examples include Rhabdoviruses, e.g. VSV; Paramyxovimses, e.g. RSV; Orthomyxovimses, e.g. influenza; Bunyaviruses and Arenaviruses), dsDNA viruses (Reoviruses, for example), RNA to DNA viruses, i.e. Retroviruses, e.g. HIV, and certain DNA to RNA viruses such as *Hepatitis* B virus.

The helicase may be purified from a natural source or may be recombinant. The helicase is usually provided in at least a partially-purified form. Only a portion of the helicase sufficient for helicase activity may be used in the present assay. Portions capable of imparting the requisite binding specificity and affinity are readily identified and produced by those skilled in the art using general molecular and biochemical methods, see e.g. Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, NY, N.Y., 1992) or that are otherwise known in the art.

The methods of the present invention require capturing unhybridized first nucleic acid or nucleic acid molecule produced by helicase activity present in the assay. Any method for capturing unhybridized first nucleic acid or nucleic acid molecule may be employed. In a preferred series of steps unhybridized first and second nucleic acids or nucleic acid molecules are incubated with a third nucleic acid or nucleic acid molecule complementary to the first nucleic acid or nucleic acid molecule and comprising a capturing ligand, under conditions where the first and third nucleic acids or nucleic acid molecules can hybridize. Thereafter, the hybridized first and third nucleic acids or nucleic acid molecules may be captured with a capturing receptor which binds the capturing ligand. The capturing receptor may be on the surface of magnetic beads in order to directly facilitate electrochemiluminescence detection.

The assay process of the present invention may be utilized in conjunction with any capturing ligand-receptor combination or system that specifically captures the first nucleic acid or nucleic acid molecule without affecting electrochemiluminescence detection. Examples of suitable ligand-receptor combinations include antibodies and their corresponding antigens. Another ligand-receptor system may be composed of protein A and immunoglobulins, or an Fc portion thereof. Additional capturing systems with which the present invention may be used include: (1) lectins-oligosaccharides or glycoproteins; (2) biotin-avidin; (3) hormone receptor-hormone; (4) enzyme-substrate or cofactor; (5) RNA-DNA; and (6) DNA-DNA. It is to be understood that in the present invention either element may serve as the ligand or receptor. In a preferred embodiment, the capturing ligand is biotin and the capturing receptor is avidin. The preparation of biotinylated oligonucleotides and of avidin-coated magnetic beads is described in Kenten et al., 1991 (*Clin. Chem.* 37:1626) and Kenten et al., 1992 (*Clin. Chem.* 38:873).

The present invention is particularly suited to screening candidate agents for the ability to modulate helicase activity, especially inhibitory activity. The invention is suitable for high-throughput drug screening of a library of candidate agents. Library-derived candidate agents encompass numerous chemical classes, though typically they are organic compounds; preferably small organic compounds. The libraries may comprise synthetic and/or naturally derived compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc., to produce structural analogs. The agent is provided in standard serial dilutions or in an amount determined by analogy to known modulators.

Typically, the present assays usually include additional reagents, such as salts, buffers, etc. to facilitate or maximize helicase activity. Also, reagents that reduce non-specific or background denaturation or otherwise improve the efficiency of the assay, such as protease inhibitors, nuclease inhibitors, antimicrobial agents, single-stranded DNA binding protein, etc. may be used.

The present invention may be better understood by reference to the following non-limiting Examples, which are provided as exemplary of the invention.

EXAMPLES

General Molecular Biology Techniques

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, protein extraction with phenol or phenol/chloroform, ethanol or isopropanol precipitation of DNA in a saline medium, transformation in Escherichia coli, and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; (2nd Ed. 1989); Ausubel F. M. et al. (eds), "Current Protocols in Molecular Biology", John Wiley & Sons, New York, 1987].

Conventional cloning vehicles include pBR322 and pUC type plasmids and phages of the M13 series. These may be obtained commercially (Bethesda Research Laboratories or New England Biolabs).

For ligation, DNA fragments may be separated according to their size by agarose or acrylamide gel electrophoresis, extracted with phenol or with a phenol/chloroform mixture, precipitated with ethanol and then incubated in the presence of phage T4 DNA ligase (Biolabs) according to the supplier's recommendations.

The filling in of 5' protruding ends may be performed with the Klenow fragment of E. coli DNA polymerase I (Biolabs) according to the supplier's specifications. The destruction of 3' protruding ends is performed in the presence of phage T4 DNA polymerase (Biolabs) used according to the manufacturer's recommendations. The destruction of 5' protruding ends is performed by a controlled treatment with S1 nuclease.

Mutagenesis directed in vitro by synthetic oligodeoxynucleotides may be performed according to the method developed by Taylor et al. [Nucleic Acids Res. 13 (1985) 8749–8764] using the kit distributed by Amersham.

The enzymatic amplification of DNA fragments by PCR [Polymerase-catalyzed Chain Reaction, Saiki R. K. et al., Science 230 (1985) 1350–1354; Mullis K. B. and Faloona F. A., Meth. Enzym. 155 (1987) 335–350] technique may be performed using a "DNA thermal cycler" (Perkin Elmer Cetus) according to the manufacturer's specifications.

Verification of nucleotide sequences may be performed by the method developed by Sanger et al. [Proc. Natl. Acad. Sci. USA, 74 (1977) 5463–5467] using the kit distributed by Amersham.

Plasmid DNAs may be purified by the Qiagen Plasmid Purification System according to the manufacture's instruction.

Example 1

Traditional helicase assay

A 60 bp oligonucleotide (5'-TTT TTT TTT TTT TTT TTT TTT TTT TTT TTT GTT AAA GGC CGC TTT TGC GGG ATC GTC ACC-3'; SEQ ID NO:1) is labeled with $^{32}$p using T4-polynucleotide kinase and then hybridized to a complementary unlabeled 60 bp oligonucleotide. The hybridized substrate and various amounts of DnaB helicase [Reha-Krantz et al. J. Biol. Chem. 253 (1978) 4043–4050; LeBowitz et al. J. Biol. Chem. 261 (1986) 4738–4748] were mixed in assay buffer (400 mM Hepes pH 7.4, 5 mM DTT, 2 mg/ml BSA, 12.5 mM MgCl$_2$, and 6.25 mM ATP) and incubated at 37° C. for 30 min. The reaction was stopped by addition of 0.5M EDTA, then 2.5 mg of Proteinase K was added to each reaction to release any remaining oligonucleotide bound to DnaB Helicase. Samples were then run on a 15% TBE gel. The single and double strands of DNA were distinguished by autoradiography.

Figure 1:
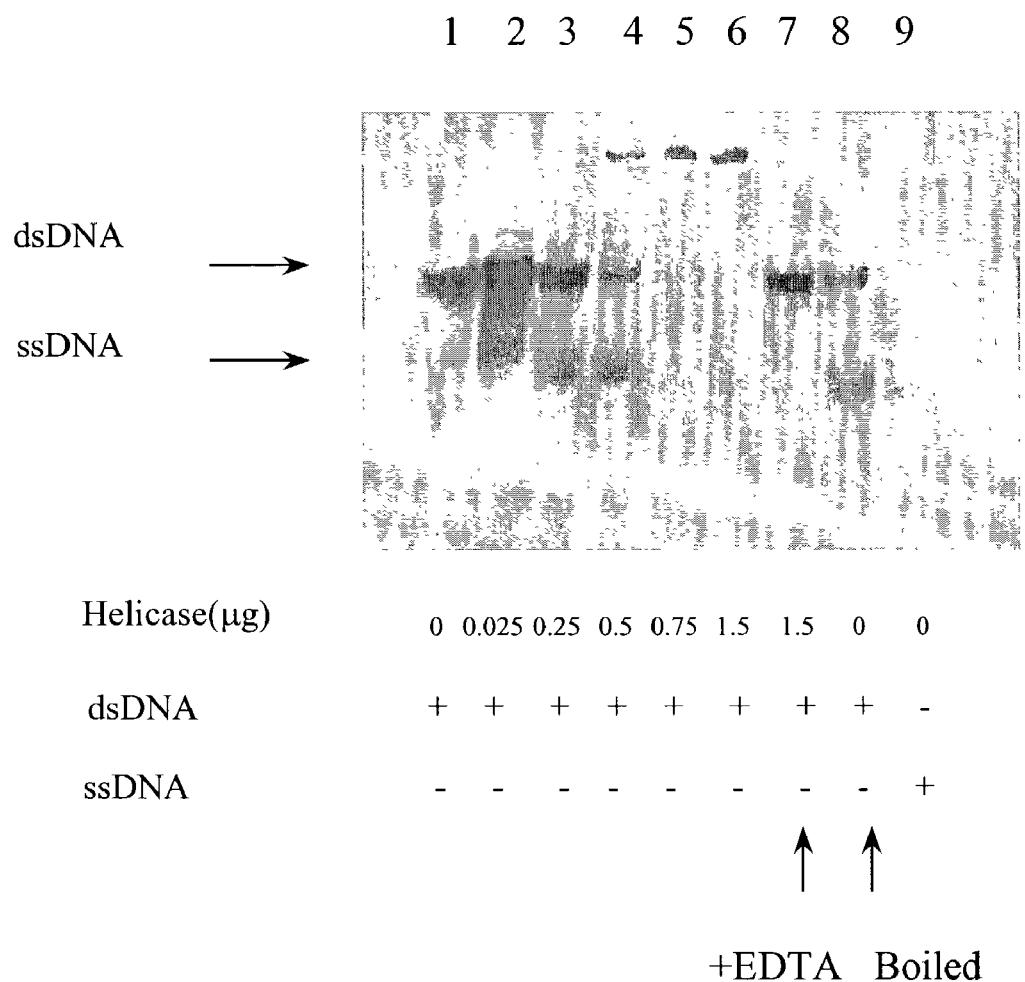
FIG. 1: Radiometric quantitation of $E.\ coli$. DnaB helicase activity.

Using the traditional helicase assay, E. coli DnaB was able to unhybridize duplex substrates to yield single strands of DNA (FIG. 1). However, to observe single-stranded DNA released from the duplex DNAs by this method, at least 0.75 ug of DnaB is required to completely unwind 175 fmol of duplex DNA substrates. Therefore, this approach is time consuming and the sensitivity is low.

Example 2

Helicase [$^3$H] Scintillation Proximity Assay (SPA) Enzyme Assay

The Scintillation Proximity Assay (SPA) is described in FIG. 2. This assay makes use of a $^3$H-oligonucleotide that is annealed to a single stranded M13 DNA (M13ssDNA). As a result of helicase activity, the $^3$H-oligonucleotide is unhybridized from the M13 ssDNA. The released oligonucleotide may then anneal to a biotinylated second oligonucleotide. This complex is captured by streptavidin coated SPA beads. Because of its close proximity to the SPA beads, the complex is able to stimulate scintillant within the beads, resulting in a signal increase. The labeled oligonucleotides that remain bound to M13 ssDNA free solution do not stimulate the scintillant.

A SPA helicase assay kit was purchased from Amersham Life Science. The assay was performed according to the provided instructions with minor modification as described below. A [$^3$H] labeled oligonucleotide is annealed with a M13 single stranded DNA (M13ssDNA) template to form partial duplex substrates. The DnaB helicase and the duplex substrates were mixed in the assay buffer and incubated at 37° C. for 45 min. The reaction is stopped with the addition of EDTA. A biotinylated complementary oligonucleotide is then annealed to the radiolabeled oligonucleotide released from M13ssDNA. The complex is captured by streptavidin coated SPA beads by incubation at room temperature for 15 min., and the radioactive signal counted.

Titration of DnaB helicase (FIG. 3) indicates that optimal activity can be obtained using 0.16 μg of DnaB helicase. Helicase activity decreases when less than 0.16 μg of DnaB is used, suggesting that there is not enough helicase to unwind the duplex DNAs. However, when more than 0.16 μg of DnaB helicase is used in each reaction, the helicase activity also decreases. This may result from non-specific binding of excess helicase to single-stranded DNAs released from the duplex DNA substrates, thereby preventing the complementary, biotinylated oligonucleotide from binding these single stranded DNA products. Under the optimal assay condition, the best signal to noise of this assay is about 10-fold (see FIG. 4). The DnaB helicase activity is 95% of the maximum possible activity, as determined by the signal generated from products released from boiled, denature duplex DNA substrates. While this method is rapid and offers the possibility of measuring a large number of samples, it is disadvantageous because of high costs and generation of significant radioactive waste.

Example 3

Fluorescence quenching helicase assay

A fluorescence quenching assay has been studied (FIG. 5). In this assay Europium- and Rhodamine-labeled probes are present as a fluorescence quenched duplex. Upon addition of a helicase, the duplex DNA substrates unhybridize to yield two single strands of DNA. The oligonucleotides labeled with Lance Europium released from the duplex substrates give rise to time resolved fluorescence signals.

A 60 bp oligonucleotide (5'-GT GAC GAT CCC GCA AAA GCG GCC TTT AAC TCC CTG CAA GCC TCA GCG ACC GAA TAT ATC G-3'; SEQ ID NO:2) was labeled with Lance-Europium at its 5' end. An oligonucleotide (5'-T TTT TTT TTT TTT TTT TTT TTT TTT TTT TTT GTT AAA GGC CGC TTT TGC GGG ATC GTC CA-3'; SEQ ID NO: 3) having a region complementary with SEQ ID NO:2 was labeled with Rhodamine at its 5' end. These Eu-labeled and Rh-labeled probes were mixed at a ratio of 1:2 and hybridized to form Y-shape substrates. Various amount of DnaB helicase and 50 fmols of the fluorescent labeled substrates were mixed in assay buffer and incubated at 37° C. for 45 min. The reaction is stopped by addition of EDTA. The fluorescence signals generated by Eu-oligonucleotides released from the duplex DNA substrates were then recorded.

Titration of DnaB helicase (FIG. 6) indicates that maximal activity requires at least 1.25 μg of DnaB helicase, and the signal to noise is about 4-fold. Together, these results show that the sensitivity of this approach is low.

Example 4

Electrochemiluminescence Helicase Assay

An electrochemiluminance (ECL) helicase assay is shown in FIG. 7. Short oligonucleotides are labeled with a Ruthenium metal chelate and annealed with M13 single strand DNAs. Upon addition of helicase, the labeled oligonucleotides are unwound from the duplex DNAs, and available to anneal to a second complementary oligonucleotide labeled with biotin. The resulting complexes are captured by streptavidin coated magnitude beads. The bead/complex is channeled through a flow cell and captured at an electrode by a magnetic field. Voltage is applied to the electrode and ECL signals derived from Ruthenium labels are measured using an electrochemiluminescence detector, such as an Origen Analyzer (IGEN Inc., Rockville, Md.).

A 60 bp oligonucleotide (5'-TTT TTT TTT TTT TTT TTT TTT TTT TTT TTT GTT AAA GGC CGC TTT TGC GGG ATC GTC ACC-3'; SEQ ID NO: 4) or a 30 bp oligonucleotide (5'- GTT AAA GGC CGC TTT TGC GGG ATC GTC ACC-3'; SEQ ID NO:5) are labeled with ruthenium at the 5' end (Kenten et al., *Clin. Chem.* 38 (1992) 873–879), and resuspended in TE buffer (10 mM Tris HCl, 1 mM EDTA, pH=7.4) to a final stock concentration of 25 pmoles/μL. M13 mp18ssDNA is dissolved in TE at a concentration of 0.183 pmoles/mL. Equal concentrations of M13mp18 ssDNA and oligonucleotides are mixed in hybridization buffer (10 mM Tris HCl, 0.3 M NaCl, 30mM Na Citrate, pH 8.5). The solution is then incubated at 100° C. for 2 minutes, and cooled to room temperature. Twenty-five fmoles of duplex substrates (M13 ssDNA annealed with 30 or 60 oligonucleotide) is mixed with 25 ng of *E. coli* DnaB helicase in assay buffer (40 mM Hepes pH 7.4, 0.5 mM DTT, 0.2 mg/ml BSA, 8 mM $MgCl_2$, 5 mM ATP). The reaction mixture is incubated at 37° C. for 45 minutes. To this reaction is added 125 fmoles of a biotinylated oligonucleotide (5'-GGT GAC GAT CCC GCA AAA GCG GCC TTT AAC AGC-3'; SEQ ID NO: 6) complementary to SEQ ID NOS: 4 and 5 in 0.5M EDTA, and the reaction is incubated at 37° C. for 15 minutes. Biotinylation is performed using the Biotin-ON™ Phosphoramidate Kit from Clontech (PT1402-1) using the procedure provided with the kit. The adenine at position 31 within SEQ ID NO:6 received the biotin label. Finally, 20 μg of streptavidin magnetic beads in a total volume of 0.25 ml TE buffer is added, and the solution is incubated for 15 minutes while vortexing. The ECL signal is recorded using an Origen Analyzer (IGEN Inc., Rockville, Md.) using conditions suggested be the manufacturer.

The data from titration of DnaB helicase indicates that only 25 ng of enzyme is required for unhybridizing 25 fmols of duplex substrates, and that the signal to noise is about 30-fold (see FIG. 8). Additional experiments demonstrate that, in general, the signal to noise is at least 30-fold, and as high as 40-fold. This method of detection shows significant sensitivity and reproducibility as compared to all previously described methods (see Table 1).

TABLE 1

Summary of SPA, Fluorescence Quenching and ECL assays

| Assay | Detection | Sensitivity (S/N) | Reagent Required Substrate (fmol) | Helicase (ug) | Decreased Sensitivity[a] |
|---|---|---|---|---|---|
| SPA | Radioactivity | ~40 | 50 | 0.16 | ~19 |
| Quenching | Fluorescence | ~4 | 50 | 1.25 | ~375 |
| ECL | Luminescence | ~30 | 25 | 0.025 | — |

[a]Relative to ECL. Calculated by multiplying the increased sensitivity (S/N) by the decreased amount of helicase necessary The sensitivity of the electrochemiluminescence assay is at least 7-fold greater than the fluorescence quenching assay and 3-fold over the SPA assay. Overall, the sensitivity is about 18-fold better than the SPA assay, and even greater when compared to the fluorescence assay. The amount of enzyme needed for electrochemiluminescence detection decreases 6-fold over the SPA assay and 50-fold over the quenching asssay. The substrates used in the electrochemiluminescence assay are reduced 2-fold compared with both the SPA and quenching assays. The electrochemiluminescence assay enables rapid and sensitive detection of helicase activity, and can be easily formatted for high throughput screening. The approach is generic, and is suitable for any enzyme having helicase activity.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:

1. A kit for electrochemiluminescent detection of helicase activity comprising:
   (a) a first nucleic acid or nucleic acid molecule comprising an electrochemiluminescent label;
   (b) a second nucleic acid or nucleic acid molecule complementary to the first nucleic acid or nucleic acid molecule; and
   (c) a helicase.

2. The kit according to claim 1, wherein the first nucleic acid or nucleic acid molecule is hybridized to the second nucleic acid or nucleic acid molecule.

3. The kit according to claim 1, further comprising a third nucleic acid or nucleic acid molecule complementary to the first nucleic acid or nucleic acid molecule.

4. The kit of claim 1, further comprising a means for capturing said first nucleic acid or nucleic acid molecule.

5. The kit of claim 4, wherein said first nucleic acid or nucleic acid molecule comprises a capturing ligand.

6. The kit according to claim 5, further comprising a capturing receptor.

7. The kit according to claim 6, wherein the capturing receptor is on the surface of magnetic beads.

8. The kit according to claim 6, wherein the capturing ligand is biotin and the capturing receptor is avidin.

* * * * *